(12) United States Patent
Woolford (10) Patent No.: US 10,293,099 B2
(45) Date of Patent: May 21, 2019

(54) PUMP AND MEANS FOR CONTROLLING A PUMP

(71) Applicant: Stryker Corporation, Kalamazoo, MI (US)

(72) Inventor: Brady L. Woolford, Mapleton, UT (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/145,315

(22) Filed: May 3, 2016

(65) Prior Publication Data

US 2016/0346454 A1    Dec. 1, 2016

Related U.S. Application Data

(60) Provisional application No. 62/166,173, filed on May 26, 2015.

(51) Int. Cl.
| | |
|---|---|
| *A61M 1/00* | (2006.01) |
| *A61M 3/02* | (2006.01) |
| *A61B 90/98* | (2016.01) |
| *A61B 18/00* | (2006.01) |
| *A61B 17/3205* | (2006.01) |
| *A61B 17/00* | (2006.01) |

(52) U.S. Cl.
CPC .......... *A61M 3/0216* (2014.02); *A61B 90/98* (2016.02); *A61M 3/0258* (2013.01); *A61B 17/3205* (2013.01); *A61B 2017/00225* (2013.01); *A61B 2018/00577* (2013.01); *A61B 2217/005* (2013.01); *A61B 2217/007* (2013.01); *A61M 1/0058* (2013.01); *A61M 2205/123* (2013.01); *A61M 2205/3331* (2013.01); *A61M 2205/3334* (2013.01); *A61M 2205/3344* (2013.01); *A61M 2205/50* (2013.01); *A61M 2205/52* (2013.01); *A61M 2205/60* (2013.01)

(58) Field of Classification Search
CPC .... A61M 3/0216; A61M 3/0258; A61B 90/98
USPC ..................... 604/500, 31, 67, 118
See application file for complete search history.

(56) References Cited

U.S. PATENT DOCUMENTS

| | | | |
|---|---|---|---|
| 6,162,194 A | 12/2000 | Shipp | |
| 7,981,073 B2 | 7/2011 | Möllstam et al. | |
| 8,192,424 B2 | 6/2012 | Woloszko | |
| 8,206,342 B2 | 6/2012 | Hacker et al. | |
| 8,608,682 B2 | 12/2013 | Möllstam et al. | |
| 8,801,654 B2 | 8/2014 | Möllstam et al. | |
| 2007/0249993 A1* | 10/2007 | Mollstam | A61B 1/015 604/65 |
| 2013/0267779 A1 | 10/2013 | Woolford et al. | |

* cited by examiner

*Primary Examiner* — Phillip A Gray
(74) *Attorney, Agent, or Firm* — Lerner, David, Littenberg, Krumholz & Mentlik, LLP (57) ABSTRACT

A pump with a controller for adjusting head pressure using a pressure boost is provided. The pressure boost may be dynamically adjusted during a surgical procedure based on the device being used and inflow and/or outflow settings.

16 Claims, 5 Drawing Sheets

PUMP AND MEANS FOR CONTROLLING A PUMP

CROSS REFERENCE TO RELATED APPLICATION

This claims the benefit of U.S. Provisional Application No. 62/166,173, filed May 26, 2015, the disclosure of which is hereby incorporated by reference in its entirety.

FIELD OF THE INVENTION

This invention relates generally to pump systems and, more particularly, to pumps and pump controlling devices and methods for surgical procedures.

BACKGROUND OF THE INVENTION

Fluid management pump systems are employed during surgical procedures to introduce sterile solution into surgical sites. One such procedure in which a fluid management pump is employed is during an endoscopic surgical procedure. In endoscopic surgery, an endoscope is inserted into the body at the site where the surgical procedure is to be performed. The endoscope is a surgical instrument that provides a view of the portion of the body in which it is inserted. Other surgical instruments are placed in the body at the surgical site. The surgeon views the surgical site through the endoscope in order to manipulate the other surgical instruments. The development of endoscopes and their companion surgical instruments has made it possible to perform minimally invasive surgery that eliminates the need to make large incisions to gain access to the surgical site. Instead, during endoscopic surgery, small openings, called portals, are formed in the patient. An advantage of performing endoscopic surgery is that since the portions of the body that are cut open are minimized, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the development of fluid management pumps. A fluid management pump is designed to pump a sterile solution into the enclosed portion of the body at which the endoscopic surgical procedure is being performed. This solution expands and separates the tissue at the surgical site so as to increase both the field of view of the surgical site and the space available to the surgeon for manipulating the surgical instruments. One type of endoscopic surgery in which fluid management pumps have proven especially useful is in arthroscopic surgery. In arthroscopic surgery, a specially designed endoscope, called an arthroscope, is employed to examine inter-bone joints and the ligaments and muscles that connect the bones. A fluid management pump is often employed in arthroscopic surgery to expand the space between the bones and adjacent soft tissue in order to increase the field in which the surgeon can perform the intended surgical procedure. Fluid management pumps are, during arthroscopic surgery, used to increase the surgical view of the joints that form an elbow, a knee, a wrist, or an ankle. Fluid management pumps are used both in endoscopic surgery and in other surgical procedures to remove debris generated by the procedure.

A fluid management pump system includes a number of different components. There is the pump unit that supplies the motive force for pumping the sterile solution through an inflow tube into the surgical site. The actuation of the pump is regulated by a control unit. The control unit receives as input signals both surgeon-entered commands and an indication of the liquid-state fluid pressure at the surgical site. Still another component of a fluid management pump system is the tube set. The tube set includes the fluid communication tubes that are connected between the pump unit, the control unit, and the surgical site in the patient which is infused with the distention fluid. The tube set includes the previously described inflow tube through which the solution is introduced into the surgical site. There is also an outflow tube through which the solution and any waste material carried therewith are removed from the surgical site. Fluid flow from the site can be regulated by a valve integral with the control unit that selectively opens and closes the outflow tube. The tube set also includes a pressure feedback tube. The pressure feedback tube provides a fluid communication path between the surgical site and the control unit so that a pressure transducer integral with the control unit can monitor the fluid pressure at the surgical site. The pressure signal the transducer supplies is used by the control unit to regulate the actuation of the pump unit and to control the open/closed state of the fluid outflow tube.

Most fluid management pump systems further include cannulae that are inserted into the patient. The cannulae function as the actual fluid communication paths between the surgical site and the tubes forming the tube set. In order to minimize the number of portals that need to be formed in the patient, a single cannula can be provided that provides both the fluid communication into the body for the inflow tube and the pressure feedback tube that functions as the guide bore through which the endoscope is inserted. These particular cannulae are called pressure sensing cannulae.

Other advantages, objects and/or purposes of the invention will be apparent to persons familiar with constructions of this general type upon reading the following specification and inspecting the accompanying drawings.

DETAILED DESCRIPTION OF PREFERRED EMBODIMENTS

For purposes of description herein, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
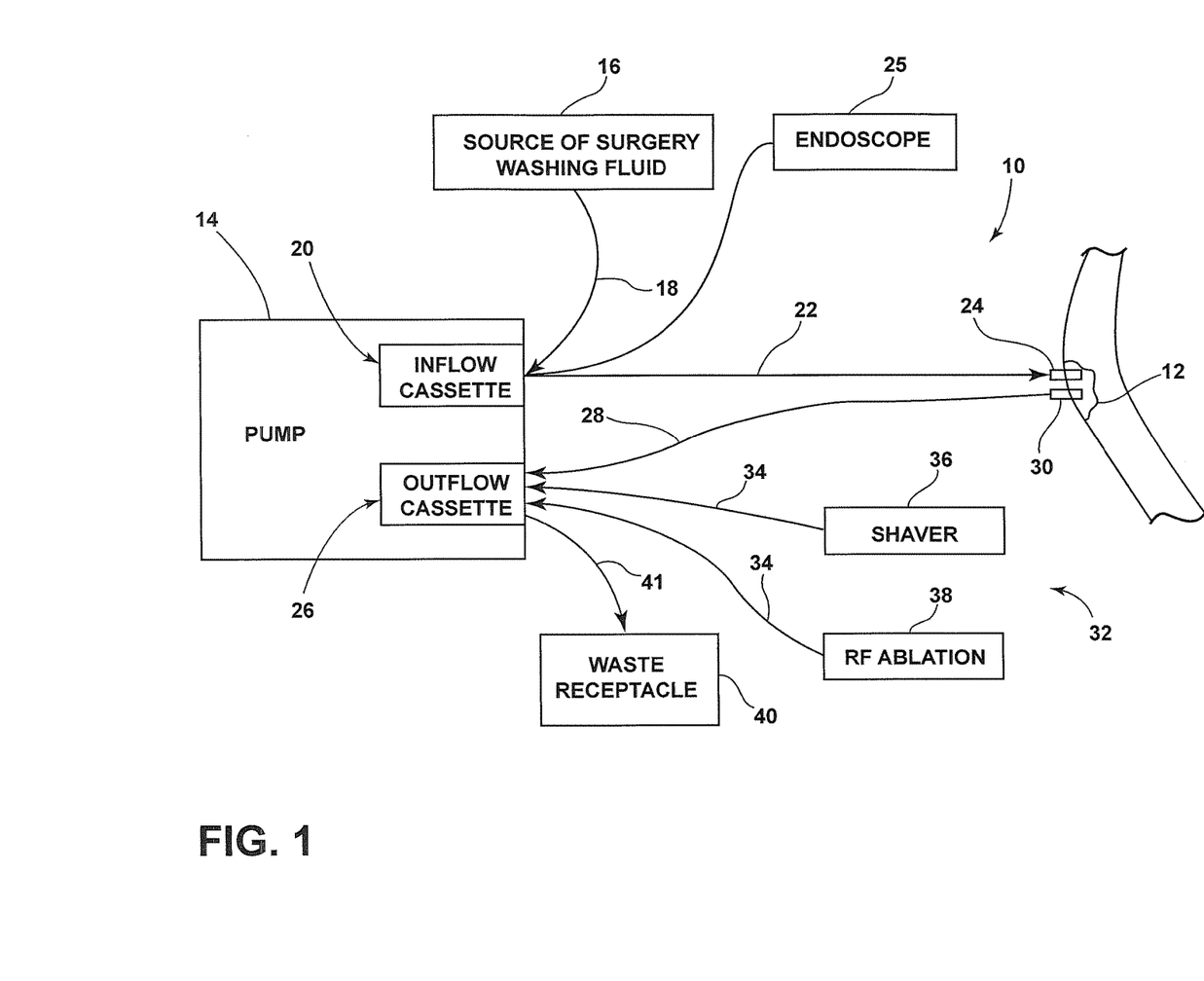
FIG. 1 is a schematic view of a pump system of the present invention illustrating flow paths through the pump system.

Referring to FIG. 1, there is illustrated a pump system 10 and flow paths through the pump system 10. The pump system 10 includes a pump 14 configured to provide a surgery washing fluid to a body cavity 12 (e.g., a joint) during surgery and to suction waste fluid out of the body cavity 12.

As illustrated in FIG. 1, the pump 14 receives a surgery washing fluid from a source of surgery washing fluid 16. The surgery washing fluid could be any washing fluid used in surgery and could be, for example, 0.9% saline or Ringer's lactate. The surgery washing fluid can provide irrigation to the body cavity 12, provide distension in a joint to give a surgeon room to operate in certain joints, and/or provide tamponade to help with bleeding. Input tubing 18 is connected between the source of surgery washing fluid 16 and the pump 14 for supplying the surgery washing fluid to the pump 14. As illustrated in FIG. 1, the pump 14 can have an inflow cassette 20 inserted therein for receiving the surgery washing fluid and for pushing the surgery washing fluid to the body cavity 12 through an inflow tube 22. Typically, the inflow tube 22 is inserted into and/or connected to an inflow cannula 24 inserted into the body cavity 12. An endoscope 25 may also be connected to the inflow cassette 20.

The illustrated pump 14 can also have an outflow cassette 26 inserted therein for suctioning the fluid out of the body cavity 12. An outflow tube 28 extends between the body cavity 12 and the outflow cassette 26, with the outflow tube 28 typically inserted into and/or connected to an outflow cannula 30 inserted into the body cavity 12. The outflow cassette 26 can also have one or more surgery devices 32 connected thereto by device suction tubing 34. The surgery devices 32 are configured to suction the fluid out of the body cavity 12 while the surgery devices 32 are being used within the body cavity 12. The surgery devices 32 can include a shaver 36, an RF ablation device 38 or any other surgery device that can suction waste fluid out of the body cavity 12. The outflow cassette 26 is connected to a waste receptacle 40 by waste tubing 41. The outflow cassette 26 works with the pump 14 to suction the waste fluid out of the body cavity 12 and to push the waste fluid into the waste receptacle 40 through the waste tubing 41. The input tubing 18, the inflow tube 22, the outflow tube 28, the device suction tubing 34, and the waste tubing 41 can have any length.

In the illustrated example, the pump system 10 can receive information from all elements of the pump system 10 to change the flow rate and/or pressure of the surgery washing fluid being provided to the body cavity 12 (i.e., inflow characteristics) and/or to change the flow rate and/or pressure of the waste fluid being suctioned from the body cavity 12 (i.e., outflow characteristics). In the illustrated example, the pump 14 and/or an integration system can contain an algorithm for altering the inflow and/or outflow characteristics. Therefore, while most of the information paths are illustrated as being between the pump 14 and other elements, the information paths could lead to the integration system instead of the pump 14. In some embodiments, the integration system is disposed within a pump housing. The pump 14 and/or integration system can include information from the body cavity 12 (e.g., pressure and temperature within the body cavity 12), the surgery devices 32 (e.g., the shaver 36 and/or the RF ablation device 38), a foot pedal, a remote control, inflow information measured within the pump 14 including pressure information of the fluid outputted from the pump 14, and outflow information measured within the pump 14 including pressure information of the fluid suctioned by the pump 14. The pump 14 can also include an input device for inputting information directly into the pump 14 (e.g., a keyboard or touch screen).

Figure 2:
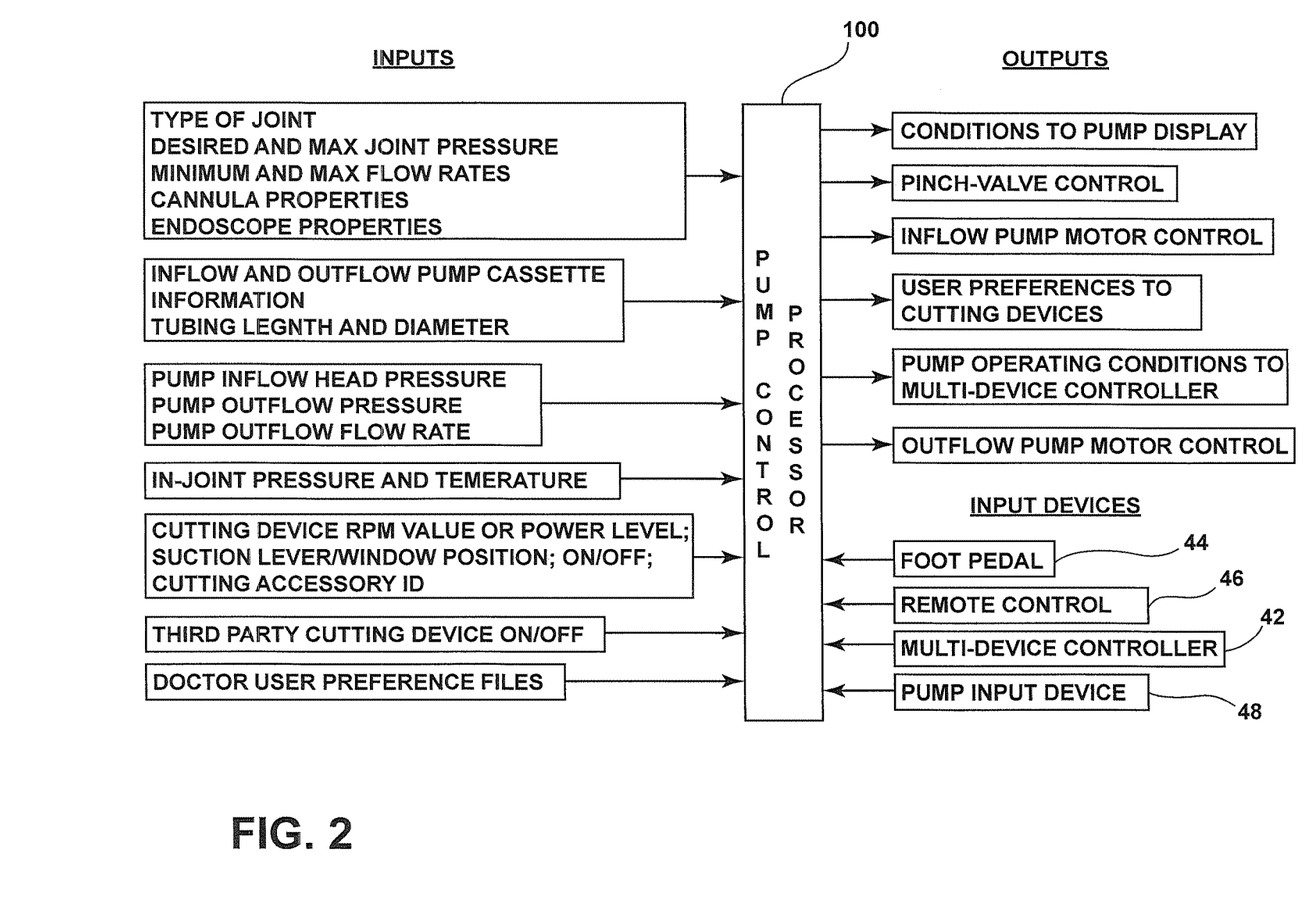
FIG. 2 is a block diagram showing inputs provided to the pump control processor and outputs from the pump control processor.

FIG. 2 illustrates various inputs, outputs and input devices that are provided with a pump control processor 100. The input devices include the multi-device operating room controller 42, a foot pedal 44, a remote control 46, and a pump input device 48.

In various embodiments, only some of the inputs shown in FIG. 2 are provided to the pump control processor 100 and only selected ones of the outputs are output therefrom. For example, in some embodiments of the invention there is no outflow pump motor control. In other embodiments, an unidentified third party surgical device is provided, wherein the pump control processor 100 does not know device parameters of such a surgical device. Many embodiments of the invention do not include an in-joint pressure sensor or an in-joint temperature sensor, and thus such directly measured joint pressure values are not provided to the pump control processor 100. In some embodiments, a multi-device operating room controller is not connected to the pump system 10. Further, additional inputs and outputs for the pump control processor 100 that are not shown in FIG. 2 are also contemplated.

In some embodiments, only inflow fluid flow control is provided by the pump 14 and the pump control processor 100 to initially maintain a constant desired in-joint pressure ($P_{joint}$) without the use of an in-joint pressure sensor. In other embodiments, inflow/outflow fluid control is provided by the pump 14 and the pump joint pressure is again maintained without an in-joint pressure sensor.

Identified Components:

In one embodiment, the type of inflow cannula 24, type of endoscope 25, and the type of inflow tube 22 and length thereof are identified. Identification information for each of the components is input into the pump control processor 100 manually or automatically. The dimensions and length of the inflow and outflow tubing, along with other properties, is typically automatically read by RF communication or identified by the pump control processor 100 when inflow and outflow tubing, via cassettes or otherwise, is inserted into the pump 14.

The pump control processor 100 utilizes stored or read dimensions and other values for the known identified components to calculate a pressure loss ($P_{loss}$) curve based on the dimensions and characteristics of the inflow tubing 22, the inflow cannula 24 and the endoscope 25 that define an inflow path to the surgical site 12 in the joint. Details for the inflow tubing, the endoscope 25 and the inflow cannula 24 can be stored in pump memory. An algorithm or program executed by the pump control processor 100 calculates coefficients ($COEF_1$ and $COEF_2$) defining the $P_{loss}$ curve from the properties including the dimensions and length of the tubing 22, and properties including dimensions of both the cannula 24 and the endoscope 25. The coefficients are provided in an equation including speed or velocity, typically revolutions per minute (RPMs) of an inflow pump motor to calculate a $P_{loss}$ value at a point on the $P_{loss}$ curve as defined for a given inflow pump motor speed.

Obtaining a $P_{loss}$ value on the $P_{loss}$ curve for an RPM value of the inflow pump motor requires an algorithm or program calculating a second order polynomial using the load coefficients $COEF_1$, $COEF_2$ as set forth in the following equation:

$$P_{loss} = COEF_1 \times (RPM\ value)^2 + COEF_2 \times (RPM\ value)$$

The above pressure loss equation results in a calculated $P_{loss}$ value at a given RPM value for the inflow motor of the pump system.

A measured head pressure ($P_{head}$) sensed by a pump inflow pressure sensor of the pump 14 disposed at or near the inflow pump cassette 20 may be used to calculate the in-joint pressure using the following equation:

$$P_{joint} = P_{head} - P_{loss}$$

Using the above calculation, the pump control processor 100 may control the inflow pump motor to maintain the $P_{joint}$ value at a generally constant predetermined desired pressure value regardless of the outflow arrangement.

The pump control processor 100 controls the inflow pump motor over a range in which there is a linear relationship between the flow rate and the inflow pump motor RPM value using the following equation:

$$Inflow = COEF_{INFL} \times (RPM\ value)$$

The inflow coefficient $COEF_{INFL}$ value is loaded from a look-up table for the identified hardware (cannula, inflow tubing, etc.) connected to the pump.

In some embodiments, an inflow cannula provides fluid to a joint without an endoscope. In such an instance, the pump control processor 100 simply determines the load coefficients and inflow coefficient from the inflow tubing and the inflow cannula. In other embodiments the cannula is an outflow cannula or a different cannula.

Unidentified Components:

Another embodiment of an inflow pump control arrangement is utilized wherein the dimensions and other properties of the inflow tubing 22, inflow cannula 24, and the endoscope 25 are unknown. In this embodiment, the pump control processor 100 utilizes a calibration routine or an algorithm as a start-up pump priming routine to obtain data values that are used to calculate the pressure loss coefficients $COEF_1$ and $COEF_2$ that define a $P_{loss}$ curve. At start-up, the pump priming routine begins. Such a routine is described in U.S. patent application Ser. No. 13/782,660, filed Mar. 1, 2013, which published as U.S. Publication No. 2013/0267779, and which is hereby incorporated by reference in its entirety. The pressure loss equation thus results in a calculated pressure loss $P_{loss}$ for a pump system having an unidentified tubing size and length, an unidentified endoscope and an unidentified cannula disposed between the pump and the surgical site of a joint.

Unlike the first embodiment discussed above, wherein the hardware such as the endoscope, the cannula, and the tubing are identified, in this embodiment pump priming execution is necessary to determine the coefficients $COEF_1$, $COEF_2$ for the second order polynomial equation defining a $P_{loss}$ curve.

Unlike the first embodiment, wherein the inflow coefficient $COEF_{INFL}$ is determined from the identified hardware, $COEF_{INFL}$ is determined from a look-up table in view of the values of coefficients $COEF_1$, $COEF_2$. In some embodiments, properties of the inflow tubing 22 may be obtained by the pump control processor 100 from the inflow pump cassette before start-up.

Recognized Surgical Device:

Surgical devices 32 manufactured by the manufacturer of the pump system 10 recognize each other's signals and thus are capable of two-way communication. Thus, performance parameters of surgical devices 32 and cutting accessories can be communicated to the pump control processor 100. In some embodiments for a shaver 36, parameters including shaver identification information and identification information including the type and size of bur or other surgical device accessory disposed on the shaver is provided automatically to the pump control processor 100. Further, the ON/OFF condition, the specific cutter or bur used, the type of operating mode selected for the shaver (examples are Forward, Reverse, Oscillation, etc.), the real-time RPM value of a shaver motor during operation, and other properties can be provided to the pump control processor 100 via the communication bus to optimize the performance of the pump 14. Further, a window size and window position of a surgical device and/or cutting accessory can be provided to the pump control processor 100.

With regard to an RF ablation device, parameters such as identification information for an RF handpiece, the ON/OFF condition thereof, the type of RF probe, identification information for the probe including suction and non-suction parameters, and the RF power level output setting can be provided automatically to the pump control processor 100 for optimizing operation of the pump 14.

In some embodiments, the dimensions of a flow path through a surgical device handpiece and the position of a lever controlling flow through the path can be provided over the communication bus to the pump control processor 100. In some embodiments surgical device identifiers and cutting accessory identifiers are sent over the communication bus to the pump control processor 100 and values for the bur size, window size, and flow path dimensions that are previously stored in the pump memory can be retrieved.

Figure 3:
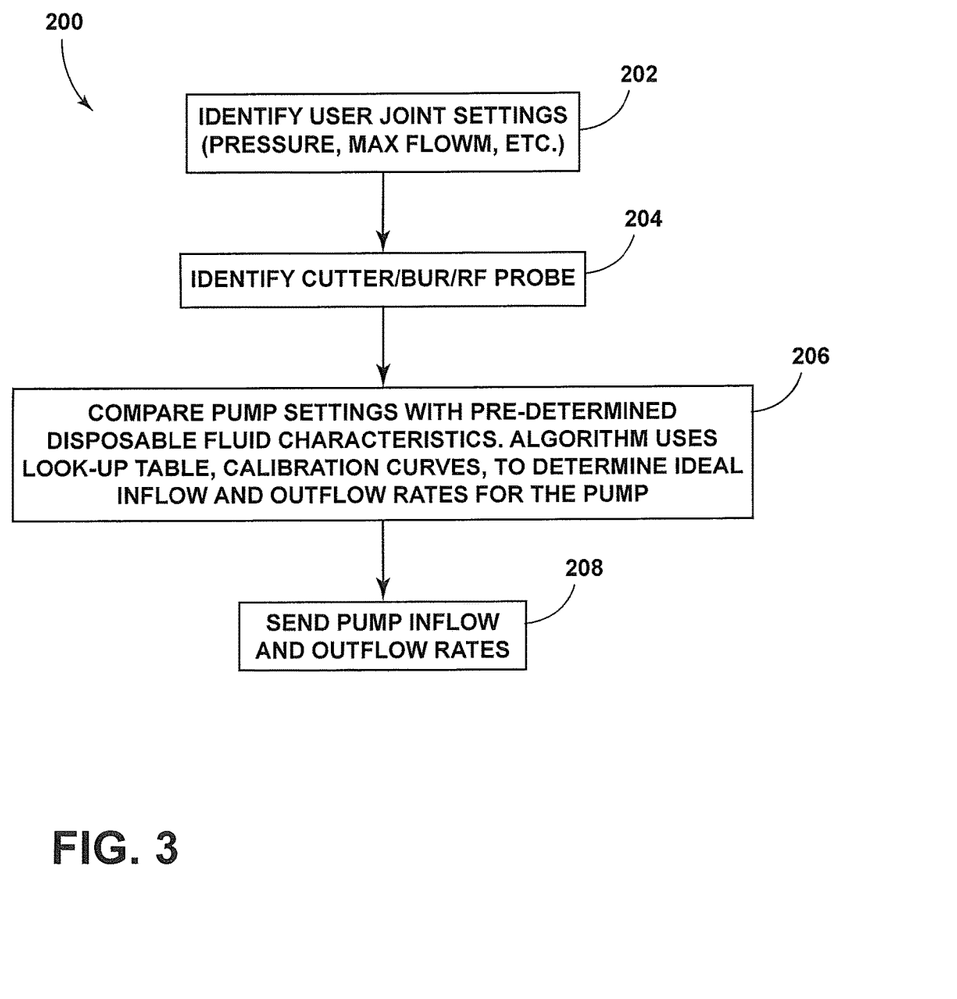
FIG. 3 is a flowchart of a portion of a pump system operating routine that includes obtaining information regarding a cutting accessory.

FIG. 3 is a flowchart of the steps of a portion of a pump flow control routine 200 executed by the pump control processor 100 that emphasizes the identification of a cutting accessory. At step 202, the type of joint, maximum and minimum flow rates, a desired or best flow rate that minimizes fluid consumption and maintains good visibility, a maximum pressure value, a desired pressure value and other types of information, including but not limited to the information or parameters listed and shown in FIG. 2, can be provided to the pump control processor 100. The information can be manually entered into the pump control processor 100 via an input device, read or downloaded automatically from a memory card or the like, or provided by other means. Then the routine advances to step 204.

At step 204 surgical device information, including identification information for a cutting accessory attached thereto, is provided to the pump control processor 100. As discussed above, the information can be provided over a communication bus. The surgical device 32 can include an RF reader to identify an RF tag secured to the cutting accessory. In another embodiment, the pump includes an RF reader to identify RF tags secured to both the surgical device and the cutting accessory. The routine then advances to step 206.

At step 206, the routine or program executed by the pump control processor 100 compares pump settings with predetermined disposable fluid flow characteristics. An algorithm or program uses a look-up table, calibration curves, and in some embodiments additional information to determine ideal fluid inflow and fluid outflow rates for operation of the pump 14. At step 208, the pump inflow control signals, and in some instances outflow information, is provided to the inflow pump motor and to additional devices to obtain ideal in-joint pressures and fluid flow at the surgical site.

A feedback path (not shown) from step 208 returns to a program or routine whereat an algorithm recalculates pump flow rates based on one or more of real-time joint pressure, inflow head pressure, pump motor speeds, surgical device speed, and ON/OFF condition. Typically, the routine does not need to re-identify the surgical device or the cutting accessory. Further, the user joint settings, such as desired joint pressure, maximum and minimum joint pressure, maximum and minimum fluid flow through the joint, and desired fluid flow information typically do not change, and thus the routine typically does not return to step 202 until one cutting operation ends and another cutting operation begins.

In one example, for a shaver operating at a motor speed of 12,000 RPM with a 5.0 mm round bur attached thereto, and a desired pressure value of 70 mmHg, the algorithm or routine executed by the pump control processor 100 provides outputs to the inflow pump motor, the outflow pump motor, and in some instances to other devices including outflow pinch valves, to obtain the desired joint pressure of 70 mmHg, while maintaining desirable inflow and outflow rates for the pump output.

When the shaver 36 is operated, the pump control processor 100 receives the ON/OFF condition and the RPM output value of the shaver and calculates and controls the inflow pump RPM value that is output by the inflow pump motor, controls the outflow pump motor, and controls pinch valves provided with or near an outflow cassette by opening a valve for the outflow tubing 34 connected to the shaver while closing a separate outflow tubing 28 from the outflow cannula 30.

The additional surgical device information, along with the joint pressure values calculated or sensed as described above, enable the pump control processor 100 of the pump 14 to more accurately control the $P_{joint}$ value and fluid flow rates that result in surgical site conditions that closely correspond to the selections or inputs of an authorized medical user operating the pump system 10.

As the shaver is identified, a non-linear outflow rate to RPM curve is provided with a look-up table containing coefficients to predict the outflow rate based on the outflow RPM for controlling the pump to provide a desired or best outflow rate. This is also the procedure for a recognized RF probe.

User preferences and other information from the pump control processor 100 can be provided to the surgical device 32, such as the shaver 36 and RF ablation device 38. The preferences can include surgical device settings preferred by the medical user that will be operating the surgical device 32 and the pump system 10.

Unrecognized Shaver and RF Ablation Surgical Devices:

The pump 14 can be utilized with unrecognized third-party surgical devices 32 that are not identifiable by the pump control processor 100. Such RF ablation devices and shaver devices are typically connected to power outlets located on the backside of the pump housing. Located within the pump housing are current and/or voltage sensing devices that sense a current waveform of the power drawn by the unrecognized surgical devices when operated. Instantaneous and past changes in the current waveform can be normalized to changes in the applied mains voltage and the pump control processor 100 can execute a linear-discrimination algorithm to optimally differentiate between times when the unidentified surgical devices are off and when the surgical devices are activated to treat or cut tissue.

As discussed above, the critical flow rate values and maximum pressure value for the surgical site 12 at the joint are typically different during operation of a surgical device 32 as compared to during non-operation of the surgical device. Therefore, sensing surgical device activation enables adjustments to the desired joint pressure value and fluid flow by control of the inflow pump motor, outflow pump motor and other devices while the surgical device is activated.

In-Joint Sensor:

In some embodiments an in-joint sensing device includes an in-joint pressure sensor and/or an in-joint temperature sensor that are disposed at or adjacent the surgical site. The in-joint sensing device can obtain and send a real-time pressure value from the surgical site 12 to the pump control processor 100, thereby avoiding reliance on the calculated $P_{loss}$ curves discussed above. The in-joint sensing device also reduces time delay in determining pressure changes in the joint. For instance, when pressure changes are measured upstream, there is a delay in the pressure change at the joint propagating through the inflow tubing to the sensor in the pump 14. The in-joint pressure sensor also removes the upstream pressure measuring influence of hydrostatic head which occurs due to height differences between the pump and the cutting accessory located at the surgical site. Therefore, the pump need not be maintained at the same level or height as the surgical site.

Overpressure:

Regardless of the type of $P_{joint}$ calculation or direct pressure measurement, a $P_{joint}$ value must not exceed a predetermined pressure value. Thus, when an overpressure condition is calculated or measured, the pump control processor 100 performs at least one of operating outflow pinch valves, reducing the RPM value of the inflow pump motor, and other steps to reduce the joint pressure.

Figure 4A:
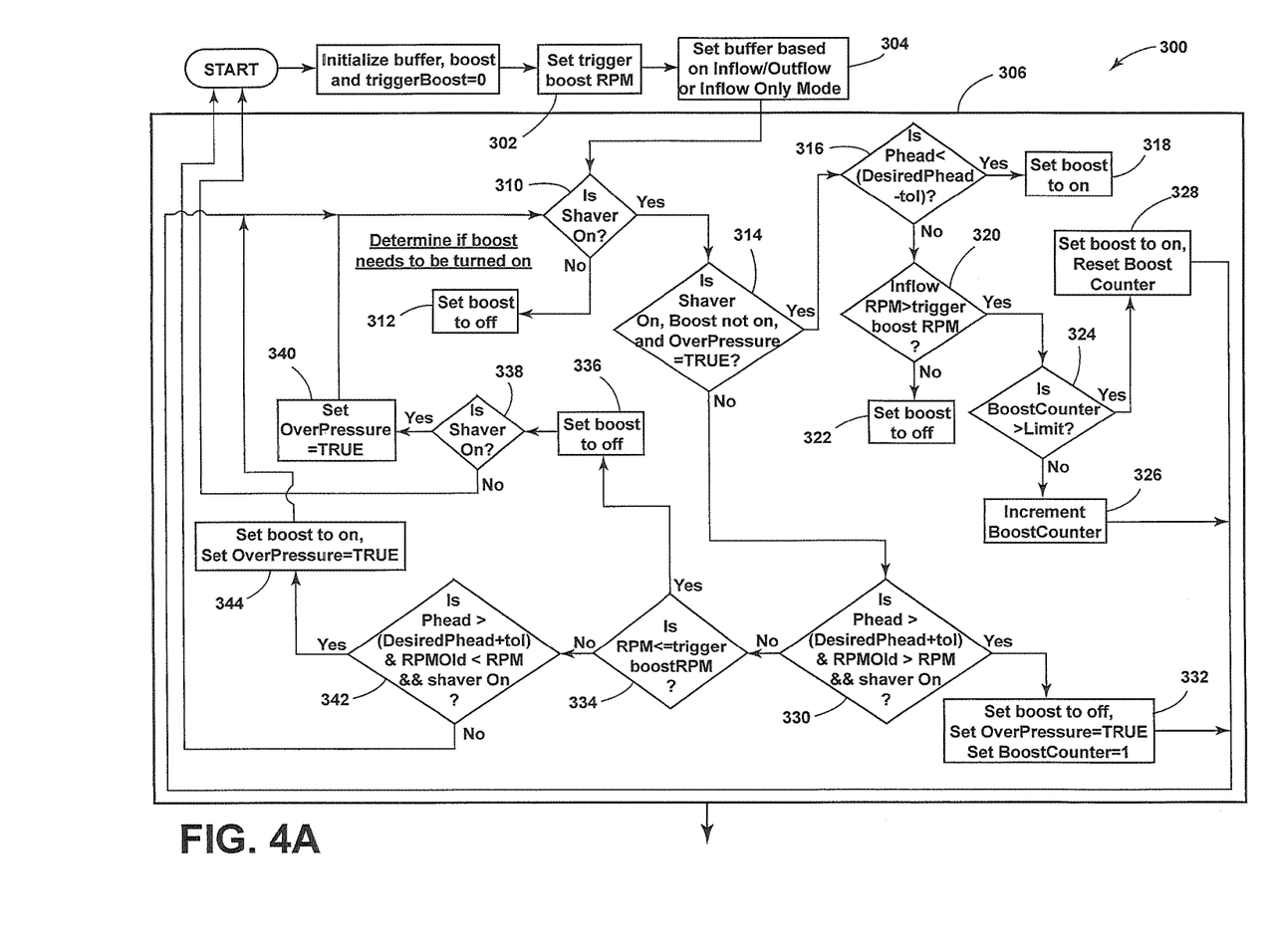
FIG. 4A is a first portion of a flowchart of a portion of a pump system operating routine that includes determining whether a boost pressure is needed.
Figure 4B:
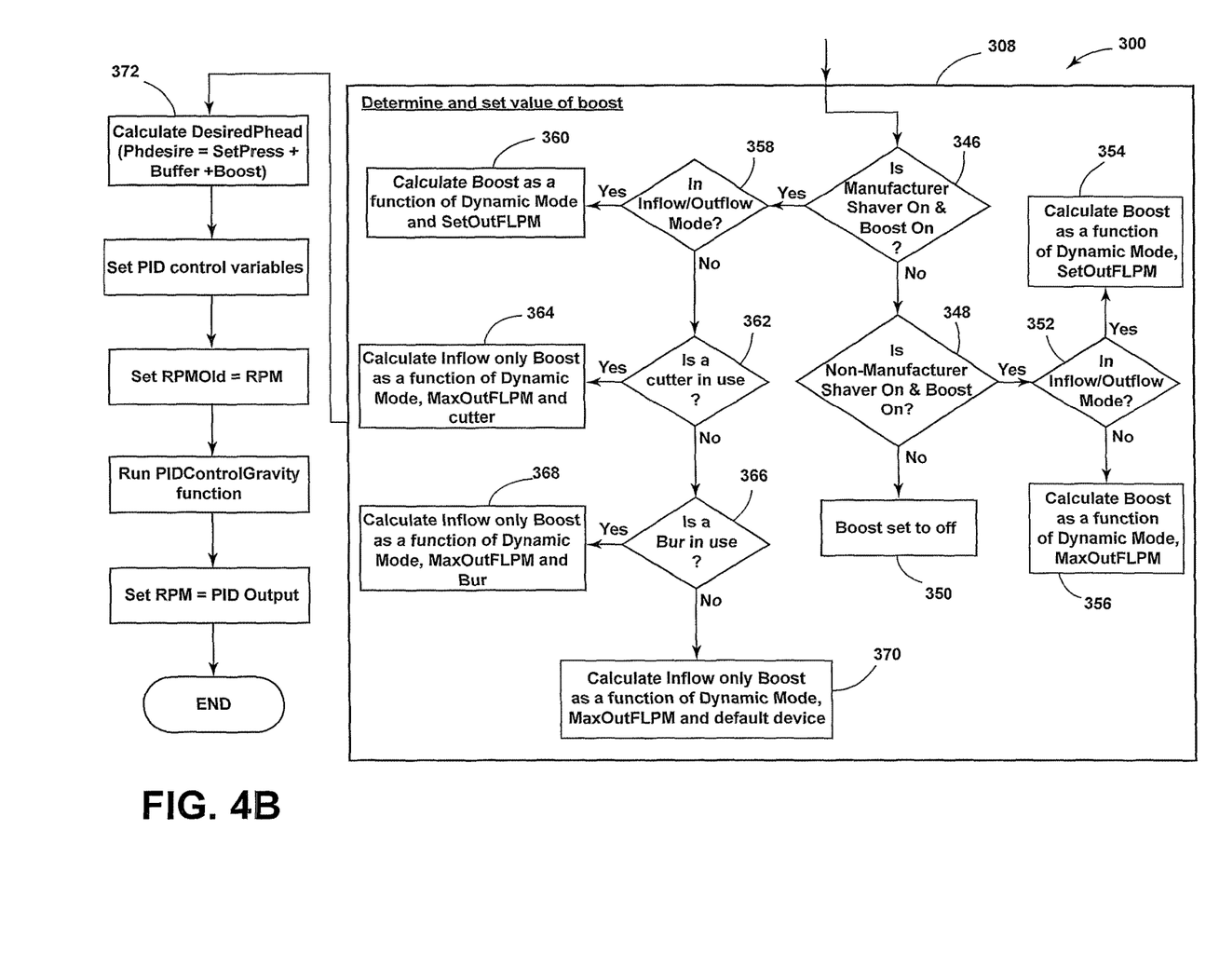
FIG. 4B is a second portion of a flowchart of a portion of a pump system operating routine that includes determining what level of boost pressure is needed to obtain a desired or appropriate head pressure.

Dynamic Adjustment of Pump Head Pressure:

An algorithm, illustrated in FIGS. 4A and 4B, may be used to control head pressure of the pump 14 during a resection procedure. This algorithm is especially useful in arthroscopy procedures and can accommodate for large pressure losses that might occur when a certain instrument such as a large bur is being used or when pressure losses are small such as when a small cutter or RF probe is being used.

As outflow increases from a surgical site such as a joint, the pressure in the site will decrease. Similar to a gravity tube set system, in this algorithm the pressure losses from the inflow hardware are no longer accounted for and the desired head pressure is used to drive the pressure in the joint. The desired head pressure can be determined as follows:

$$P_{head} = P_{set} + P_{offset} + P_{boost}$$

where $P_{set}$ is the pressure that the user sets on the graphic user interface on the stand alone control module. $P_{offset}$ is applied and is typically a function of $P_{set}$. $P_{boost}$ is the pressure that is added or removed from the desired head pressure when a resection device is activated. The algorithm illustrated in FIGS. 4A and 4B is used to dynamically adjust the $P_{boost}$ value shown in the above equation.

Referring now to FIG. 4A, the first part of the $P_{boost}$ algorithm 300 is illustrated. Once the algorithm is started and initialized, the trigger boost RPM, i.e., the pump RPM for the inflow, is set, as shown in step 302. Then, step 304 is performed in which the buffer is set based on whether the system is in the Inflow/Outflow mode or in the Inflow Only mode. This typically means the system recognizes whether both an inflow and outflow cassette are being utilized or whether only an inflow cassette is being utilized.

After such values are set, step 306 is performed, during which it is determined if the boost needs to be turned on (either in a positive or negative manner). Step 306, which is discussed in detail below, is followed by step 308 in which the value of the boost is determined and set.

Step 306, shown in FIG. 4A, utilizes a decision tree with a number of factors for determining properly whether the boost needs to be turned on. The first condition to be considered in step 306 is whether the shaver is on, as shown in substep 310. The term "shaver" used herein is used generically to refer to any surgical, resection, or ablation device used with the pump system 10. If the shaver is not on, the boost is set to OFF, as shown at substep 312, and the algorithm moves to step 308. If it is determined that the shaver is on (i.e., that the answer to the question is "YES"), the algorithm moves to substep 314 at which it is determined if all of the following are true: The shaver is on, the boost is not on, and the overpressure equals TRUE (meaning that the $P_{joint}$ value exceeds a predetermined pressure value).

If all of the conditions of substep 314 are true, (i.e., the decision result is "YES"), the algorithm then moves to substep 316. At substep 316 it is determined whether the $P_{head}$ is less than the desired $P_{head}$ minus a set tolerance level. If the head pressure is less than the desired head pressure minus the tolerance level, then the boost is set to ON at substep 318 and the algorithm moves to step 308. However, if the answer to substep 316 is "NO," the algorithm moves to substep 320 at which it is determined whether the current inflow RPM is greater than the trigger boost RPM. If the answer to decision substep 320 is "NO," the algorithm moves to substep 322 at which the boost is set to OFF and the algorithm then moves on to step 308. If the inflow RPM is greater than the trigger boost RPM (i.e., the answer is "YES"), the algorithm then moves to substep 324 at which it is determined whether the boost counter is greater than a predetermined limit for the boost counter. If not, the boost counter is then incremented (for example, one is added to the counter) at substep 326 and the algorithm then returns to substep 310. If the boost counter is over the limit (i.e., the answer to the question is "YES"), then the algorithm moves to substep 328 at which the boost is set to ON, and the boost counter is reset. The algorithm then returns to substep 310.

If the answer to substep 314 is "NO" then the algorithm moves to substep 330 at which it is determined whether the $P_{head}$ head is greater than the desired $P_{head}$ plus any tolerance allowed, and whether the old RPM is greater than the current RPM, and whether the shaver is on. If all three of these conditions are met (i.e., the answer is "YES"), then the boost is set to OFF, the overpressure is set to TRUE, the boost counter is set to 1, and the algorithm returns to substep 310. If the answer to decision substep 330 is "NO" (i.e., at least one of the conditions is not met), then the algorithm moves to substep 334. At substep 334, it is determined whether the current RPM is less than or equal to the trigger boost RPM. If the answer to this condition is "YES" then the algorithm moves to substep 336 at which the boost is set to OFF, and moves to substep 338. At substep 338, it is determined whether the shaver is on. If the answer to this is "YES," the algorithm moves to substep 340 at which the overpressure is set to TRUE and the algorithm returns to substep 310. If the answer to the decision substep 338 is "NO," then the algorithm returns to its start.

If the answer to decision substep 334 is "NO" (i.e., current RPM is not less than or equal to the trigger boost RPM), then the algorithm moves to substep 342. At substep 342 it is determined whether the $P_{head}$ is greater than the desired $P_{head}$ minus any allowable tolerance, and whether the old RPM value is less than the current RPM value, and whether the shaver is ON. If all of these conditions are met (i.e., the answer is "YES"), then the algorithm moves on to substep 344 at which the boost is set to ON and the overpressure is set to TRUE, followed by the algorithm returning to step 310. If the answer to the conditions of substep 342 is "NO" then the algorithm returns to its start.

At step 308, the value of the boost is determined generally by determining the type of instrument being used and whether the system is in an Inflow/Outflow mode or not. At step 308, the algorithm first determines, at substep 346, whether a shaver made by the manufacturer of the pump system is ON and whether the boost is ON. If the answer is "NO," the algorithm proceeds to substep 348 at which is determined whether a shaver is ON that is not of the pump system manufacturer and whether the boost is ON. If the answer to this decision substep is "NO," then the algorithm moves to step 350 at which the boost is set to OFF. If the answer to the conditions of substep 348 is "YES" then the algorithm moves to step 352 at which it is determined whether the system is in the Inflow/Outflow mode. If "YES," then the algorithm moves to step 354 at which the boost is calculated as a function of the dynamic mode and a set outflow value. If the answer to the decision of substep 352 is "NO" then the algorithm moves to substep 356 at which the boost is calculated as a function of the dynamic mode and the maximum outflow value from a lookup table for the particular shaver.

If the answer to substep 346 is "YES" (i.e., that a shaver of the pump manufacturer is ON and the boost is ON), the algorithm proceeds to substep 358. At substep 358, it is determined whether the system is in the Inflow/Outflow mode or not. If the answer to substep 358 is "YES" (i.e., that the system is in the Inflow/Outflow mode), then the algorithm proceeds to substep 360, at which the boost is calculated as a function of the dynamic mode and the set outflow.

If the system is not in the Inflow/Outflow mode (i.e., the answer to the decision of substep 358 is "NO"), the algorithm proceeds to substep 362 which determines whether a cutter is in use. If a cutter is in use (i.e., the answer to substep 362 is "YES"), then the algorithm moves to substep 364. At substep 364, the boost is calculated as an inflow only value as a function of dynamic mode and the maximum outflow based on data for a cutter.

If a cutter is not in use (i.e., the answer to substep 362 is "NO"), then the algorithm proceeds to substep 366, at which it is determined whether a bur is in use. If a bur is in use (i.e., the question to the decision substep 366 is "YES"), then the algorithm proceeds to step 368. At substep 368, the boost is calculated as an inflow only value as a function of dynamic mode and the maximum outflow based on data for a bur. If the answer to substep 366 is "NO" (i.e., a bur is not in use), then the system does not recognize the device and the algorithm moves to substep 370 at which the boost is calculated as an inflow only value as a function of dynamic mode and the maximum outflow for a default device which is set in the code of the algorithm.

Once the value of boost is determined in step 308, the algorithm proceeds to step 372, at which the desired $P_{head}$ is calculated using the $P_{head}$ formula given above. PID control variables are set, the old RPM is set to the current RPM value, and the RPM value is set to the PID output value.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of controlling a pump to adjust pressure at a surgical site, the method comprising:

providing a pump for motivating a flow of fluid to a surgical site;
providing a pump controller which has the capability of receiving flow information and causing the pump to provide a pressure boost;
providing a surgical device in communication with the pump controller;
providing a set head pressure which is communicated to the pump controller;
activating the surgical device;
wherein the pump controller executes the following steps:
  (a) receiving information from the surgical device in communication with the pump controller;
  (b) using the information provided by the surgical device to determine a desired surgical site pressure and a surgical site fluid flow rate, and using the desired surgical site pressure and surgical site fluid flow rate to determine whether a pressure boost is needed to be added to or subtracted from the set head pressure to result in an appropriate pressure at the surgical site;
  (c) if a pressure boost is needed, calculating the amount of pressure boost needed by using the information provided by the surgical device;
  (d) adjusting the pump flow to a level at which the amount of pressure boost needed is achieved.

2. The method of claim 1, wherein the information provided by the surgical device and which is used by the pump controller to determine whether a pressure boost is needed comprises at least the type of surgical device.

3. The method of claim 1, wherein the flow information includes the mode of inflow and outflow and is used by the pump controller in calculating the amount of pressure boost needed.

4. The method of claim 1, wherein if the surgical device is not on, the pump controller determines that a pressure boost is not needed.

5. The method of claim 1, wherein information concerning the type of surgical device is used in calculating the amount of pressure boost needed.

6. The method of claim 1, wherein information concerning whether the surgical device is manufactured by the manufacturer of the pump is used in calculating the amount of pressure boost needed.

7. The method of claim 1, wherein the pump controller has a look-up table for information concerning surgical devices to be used to calculate the amount of pressure boost needed.

8. The method of claim 1, wherein if the pump system is not in an Inflow/Outflow mode, a maximum outflow value is used in calculating the amount of pressure boost needed.

9. The method of claim 1, wherein if the pump system is in an Inflow/Outflow mode, a set outflow value is used in calculating the amount of pressure boost needed.

10. A method of controlling a pump to adjust pressure at a surgical site, the method comprising:
providing a pump for motivating fluid to a surgical site;
providing a pump controller which has the capability of causing the pump to provide a pressure boost;
providing a surgical device in communication with the pump controller;
providing a set head pressure which is communicated to the pump controller;
providing a set trigger boost flow rate which is communicated to the pump controller;
the pump controller determining if the surgical device is activated;
if the surgical device is activated, the pump controller determining whether a pressure boost is currently being delivered and whether the site is in an overpressure state;
if the surgical device is activated, a pressure boost is currently being delivered and the site is in an overpressure state, the pump controller determining if a pressure boost is needed based at least on the current head pressure in relation to the desired head pressure;
if at least one of the surgical device is activated, a pressure boost is currently being delivered, and the site is in an overpressure state is not true, the pump controller determining if a pressure boost is needed based at least on the current head pressure in relation to the desired head pressure and a prior flow rate in relation to the current flow rate;
once it is determined whether a pressure boost is needed, the pump controller calculating the needed pressure boost by using the information provided by the surgical device and whether the system is in an Inflow/Outflow mode;
the pump controller adjusting the pump flow rate to a level at which the amount of pressure boost needed is achieved,
wherein the pump has a manufacturer, and the information provided by the surgical device includes whether the surgical device is manufactured by the pump manufacturer.

11. A method of controlling a pump to adjust pressure at a surgical site, the method comprising:
providing a pump for motivating fluid to a surgical site;
providing a pump controller which has the capability of causing the pump to provide a pressure boost;
providing a surgical device in communication with the pump controller;
providing a set head pressure which is communicated to the pump controller;
providing a set trigger boost flow rate which is communicated to the pump controller;
the pump controller determining if the surgical device is activated;
if the surgical device is activated, the pump controller determining whether a pressure boost is currently being delivered and whether the site is in an overpressure state;
if the surgical device is activated, a pressure boost is currently being delivered and the site is in an overpressure state, the pump controller determining if a pressure boost is needed based at least on the current head pressure in relation to the desired head pressure;
if at least one of the surgical device is activated, a pressure boost is currently being delivered, and the site is in an overpressure state is not true, the pump controller determining if a pressure boost is needed based at least on the current head pressure in relation to the desired head pressure and a prior flow rate in relation to the current flow rate;
once it is determined whether a pressure boost is needed, the pump controller calculating the needed pressure boost by using the information provided by the surgical device and whether the system is in an Inflow/Outflow mode;
the pump controller adjusting the pump flow rate to a level at which the amount of pressure boost needed is achieved, wherein the pump controller increments a boost counter until the boost counter reaches a predetermined boost counter limit, at which time the boost is turned on.

12. The method of claim 1, wherein the flow information includes an inflow RPM value.

13. The method of claim 12, and further including the step of determining whether the inflow RPM value is greater than a predetermined trigger boost RPM.

14. The method of claim 13, wherein if the inflow RPM value is not greater than the trigger boost RPM, the pressure boost is set to OFF.

15. The method of claim 1, and further including the step of determining whether the surgical device is activated.

16. The method of claim 15, wherein if it is determined that the surgical device is not activated, either returning to the step of receiving information from the surgical device or setting the pressure boost to OFF.

* * * * *